United States Patent [19]

Squaratti

[11] 4,435,576

[45] Mar. 6, 1984

[54] PROCESS FOR THE PRODUCTION OF 2-AMINO-4-METHYL-BENZOTHIAZOLE

[75] Inventor: Armand Squaratti, Brig, Switzerland

[73] Assignee: Lonza Ltd., Gampel, Switzerland

[21] Appl. No.: 248,455

[22] Filed: Mar. 27, 1981

Related U.S. Application Data

[63] Continuation of Ser. No. 103,540, Dec. 13, 1979, abandoned.

[30] Foreign Application Priority Data

Dec. 20, 1978 [CH] Switzerland .................. 12931/78

[51] Int. Cl.³ .............................................. C07D 277/82
[52] U.S. Cl. ................................................... 548/164
[58] Field of Search ......................................... 548/164

[56] References Cited

U.S. PATENT DOCUMENTS

| 1,911,085 | 5/1933 | Lubs | 548/164 |
| 1,984,885 | 12/1934 | Lubs et al. | 548/164 |
| 4,035,379 | 7/1977 | Fuchs | 548/164 |

OTHER PUBLICATIONS

The New Encyclopedia Britannica, Micropaedia, vol. 1, p. 247 (1974).
Jackson et al., J. Chem. Soc. (C), (1969), pp. 268–272.

*Primary Examiner*—Paul M. Coughlan, Jr.
*Assistant Examiner*—D. B. Springer
*Attorney, Agent, or Firm*—Fisher, Christen & Sabol

[57] ABSTRACT

Process for the production of 2-amino-4-methylbenzothiazole from o-tolylthiourea using chlorine as a ring closure reactant. The reaction is carried out without a catalyst. By the use of methylene chloride as a solvent, no ring chlorination takes place. The product is removed from the resultant HCl-salt form by treatment with sodium hydroxide solution.

20 Claims, No Drawings

PROCESS FOR THE PRODUCTION OF 2-AMINO-4-METHYL-BENZOTHIAZOLE

This is a continuation of application Ser. No. 103,540, filed Dec. 13, 1979, now abandoned.

BACKGROUND OF THIS INVENTION

1. Field of the Invention

This invention relates to the production of 2-amino-4-methylbenzothiazole.

2. Prior Art

The production of aminobenzothiazole from phenylthioureas with chlorine in aprotic solvents in the presence of catalytic quantities of bromine or preferably iodine is described in French Patent Application No. 2,357,533. According to the U.S. Pat. No. 1,984,885, the conversion to benzothiazoles with chlorine alone leads to products which are likewise chlorinated in the benzol (benzene) ring.

BROAD DESCRIPTION OF THIS INVENTION

An object of this invention is to provide a simple, efficient and economical process for the production of 2-amino-4-methylbenzothiazole with chlorine as a ring closure reactant without the use (presence) of a catalyst. Other objects and advantages of this invention are set out herein or are obvious herefrom to one ordinarily skilled in the art.

The objects and advantages of this invention are achieved by the process of this invention.

Broadly, this invention involves a process for the production of 2-amino-4-methylbenzothiazole from o-tolylthiourea using chlorine as a ring closure reactant. The reaction is carried out without a catalyst. By the use of methylene chloride as a solvent, no ring chlorination takes place during the reaction.

The reaction according to this invention is shown by the following formula:

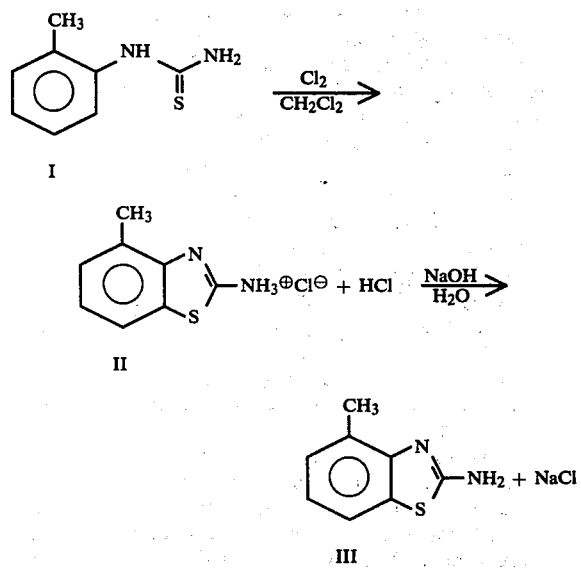

o-tolylthiourea (I) can be produced in a known manner from o-toluidine and ammonium rhodanate or sodium rhodanate. One weight unit of the o-tolylthiourea is suspended in 3 to 40 times dilution (volume basis) of methylene chloride. The suspension is cooled to a temperature between $-20°$ and $+15°$ C. Chlorine in quantities of 1 to 2 moles, related to one mole of o-tolylthiourea, is introduced into the mixture while stirring. The hydrochloric acid, which is formed by the reaction, separated from the 2-amino-4-methylbenzothiazole—preferably it is removed by boiling at reflux for 1 to 2 hours. After completion of the hydrochloric acid development (and removal), the 2-amino-4-methylbenzothiazole hydrochloride (II) is filtered off. The hydrochloride is converted in water with a base or an alkali, preferably with caustic soda (NaOH) solution, into 2-amino-4-methylbenzothiazole (III) and the latter is filtered off. The base can be any suitable base, such as, inorganic bases, e.g., alkaline earth hydroxides or alkali metal hydroxides specific examples are sodium hydroxide, ammonium hydroxide, beryllium hydroxide, calcium hydroxide, lithium hydroxide, potassium hydroxide and zinc hydroxide. Other examples of bases are hydrazine, hydroxlamine and sodium oxide.

The product, produced by the process of this invention, is free of impurities and is obtained as a white crystalline powder in a high yield.

The process according to this invention permits the production of 2-amino-4-methylbenzothiazole without the use of any or an additional catalyst which, on its part, would have to be removed from the reaction mixture and isolated. A chlorination on the benzene (benzol) ring does not take place, despite the absence of a catalyst.

DETAILED DESCRIPTION OF THIS INVENTION

As used herein, all percentages and ratios are on a weight basis unless otherwise specified hereon or obvious herefrom to one ordinarily skilled in the art. The following example is the preferred embodiment of this invention.

EXAMPLE 73.5 g of o-tolylthiourea, produced according to a known process, was suspended in 375 ml of methylene chloride, and the suspension was cooled to about 1° C. While stirring, 32.5 g of chlorine gas was conducted through a gas introduction pipe into the reaction mixture. The 2-amino-4-methylbenzothiazole hydrochloride was crystallized out, whereby the hydrochloric acid development (removal) started. After completion of the hydrochloric acid removal by boiling at a reflux temperature, the reaction mixture was drained off and dried. The yield amounted to 85.0 g, which corresponds to 95.8 percent of 2-amino-4-methylbenzothiazole hydrochloride.

Upon treating the hydrochloride with an aqueous caustic soda (NaOH) solution, 67.3 g (96.8 percent) of 2-amino-4-methylbenzothiazole was obtained.

What is claimed is:

1. Process for the production of 2-amino-methylbenzothiazole comprising the steps of:
   (a) reacting o-tolylthiourea with chlorine, a ring closure reactant, in the presence of methylene chloride and in the absence of a catalyst, there being no chlorination of the benzene ring in the o-tolylthiourea, 2-amino-4-methylbenzothiazole hydrochloride resulting, one weight unit of o-tolylthiourea being used per 3 to 40 volume units of methylene chloride, 1 to 2 moles of chlorine being used per mole of o-tolylthiourea, step (a) being conducted at a temperature between $-20°$ and $+15°$ C., the methylene chloride being a suspending liquid and a solvent for the o-tolylthiourea, being a suspending agent for the 2-amino-4-methyl-benzothiazole hydrochloride and being a solvent for the chlorine; and (b) reacting the 2-amino-4-methylbenzothiazole hydrochloride with a sufficient amount of a base, 2-amino-4-methylbenzothiazole resulting, said base being selected from the group consisting of an alkali metal hydroxide, an alkaline earth metal hydroxide, hydrazine, hydroxylamine, sodium oxide, ammonium hydroxide and zinc hydroxide.

2. Process as claimed in claim 1 wherein the o-tolylthiourea, before step (a), is mixed with methylene chloride to form a suspension, the suspension being formed at room temperature and cooled to a temperature between −20° and +15° C. before step (a) is conducted, wherein the hydrochloric acid, produced as a by-product in step (a), is separated from the 2-amino-4-methylbenzothiazole hydrochloride before step (b) wherein the 2-amino-4-methylbenzothiazole hydrochloride is separated, after the hydrochloric acid removal, from the reaction medium of step (a), wherein the 2-amino-4-methylbenzothiazole is separated from the reaction medium of step (b) after step (b) is completed.

3. Process as claimed in claim 2 wherein step (a) is conducted with stirring, wherein the hydrochloric acid is separated by boiling at reflux, wherein the 2-amino-4-methylbenzothiazole hydrochloride, after the hydrochloric acid separation, is separated from the reaction medium of step (a) before step (b) by filtration, and wherein the separation of the 2-amino-4-methylbenzothiazole from the reaction medium of step (b), after step (b) is completed, is achieved by filtration.

4. Process as claimed in claim 2 wherein the base used in step (b) is sodium hydroxide.

5. Process as claimed in claim 3 wherein said base is sodium hydroxide, beryllium hydroxide, calcium hydroxide, lithium hydroxide or potassium hydroxide.

6. Process for the production of 2-amino-4-methylbenzothiazole consisting essentially of the steps of:

(a) mixing o-tolylthiourea with methylene chloride to form a suspension, the methylene chloride also being a solvent for the o-tolylthiourea the suspension being formed at room temperature, and cooled to a temperature between −20° and +15° C.;

(b) reacting the o-tolylthiourea with chlorine, a ring closure reactant, in the presence of the methylene chloride and in the absence of a catalyst, there being no chlorination of the benzene ring in the o-tolylthiourea, 2-amino-4-methylbenzothiazole hydrochloride resulting, one weight unit of o-tolylthiourea being used per 3 to 40 volume units of methylene chloride, 1 to 2 moles of chlorine being used per mole of o-tolylthiourea, step (b) being conducted with stirring, and step (b) being conducted at a temperature between −20° and +15° C., the methylene chloride being a solvent for the chlorine and being a suspending liquid for the 2-amino-4-methylbenzothiazole hydrochloride;

(c) separating the hydrochloric acid, produced as a byproduct in step (b), from the 2-amino-4-methylbenzothiazole hydrochloride;

(d) removing the 2-amino-4-methylbenzothiazole hydrochloride, after the hydrochloric acid removal, from the reaction medium of step (b) by filtration; and (e) reacting the 2-amino-4-methylbenzothiazole hydrochloride with a sufficient amount of a base, 2-amino-4-methylbenzothiazole resulting, said base being selected from the group consisting of an alkali metal hydroxide, an alkaline metal earth hydroxide, hydrazine, hydroxylamine, sodium oxide, ammonium hydroxide and zinc hydroxide.

7. Process as claimed in claim 6 wherein the o-tolylthiourea, before step (b), is mixed with methylene chloride to form a suspension, the suspension being formed at room temperature and cooled to a temperature between −20° and +15° C. before step (b) is conducted, wherein the hydrochloric acid, produced as a by-product in step (b), is separated from the 2-amino-4-methylbenzothiazole hydrochloride befoe step (e), wherein the 2-amino-4-methylbenzothiazole hydrochloride is separated, after the hydrochloric acid removal, from the reaction medium of step (b), wherein the base used in step (e) is in aqueous solution form, and wherein the 2-amino-4-methylbenztothiazole is separated from the reaction medium of step (e) after step (e) is completed.

8. Process as claimed in claim 7 wherein step (b) is conducted with stirring, wherein the hydrochloric acid is separated by boiling at reflux, wherein the 2-amino-4-methylbenzothiazole hydrochloride, after the hydrochloric acid separation, is separated from the reaction medium of step (b) before step (e) by filtration, and wherein the separation of the 2-amino-4-methylbenzothiazole from the reaction medium of step (e) after step (e) is completed is achieved by filtration.

9. Process as claimed in claim 7 wherein the base is an alkali metal hydroxide.

10. Process as claimed in claim 7 wherein the base is an alkaline earth metal hydroxide.

11. Process as claimed in claim 7 wherein the base is sodium hydroxide, beryllium hydroxide, calcium hydroxide, lithium hydroxide or potassium hydroxide.

12. Process for the production of 2-amino-4-methylbenzothiazole consisting essentially of the steps of:

(a) mixing the o-tolylthiourea with methylene chloride to form a suspension, the methylene chloride also being a solvent for the o-tolythiourea;

(b) reacting the o-tolylthiourea with chlorine, a ring closure reactant, in the presence of the methylene chloride and and in the absence of a catalyst, there being no chlorination of the benzene ring in the o-tolylthiourea, 2-amino-4-methylbenzothiazole hydrochloride resulting, one weight unit of o-tolylthiourea being used per 3 to 40 volume units of methylene chloride, 1 to 2 moles of chlorine being used per mole of o-tolylthiourea, step (b) being conducted at a temperature between −20° and +15° C., the methylene chloride being a solvent for the chlorine and being a suspending liquid for the 2-amino-4-methyl-benzothiazole hydrochloride; and (c) reacting the 2-amino-4-methylbenzothiazole hydrochloride with a sufficient amount of a base, 2-amino-4-methyl benzothiazole resulting, said base being selected from the group consisting of an alkali metal hydroxide, an alkaline metal hydroxide, hydrazine, hydroxylamine, sodium oxide, ammonium hydroxide and zinc hydroxide.

13. Process as claimed in claim 12 wherein the o-tolythiourea, before step (a), is mixed with methylene chloride to form a suspension, the suspension being formed at room temperature and cooled to a temperature between −20° and +15° C. before step (a) is conducted, wherein the hydrochloric acid, produced as a byproduct in step (a), is separated from the 2-amino-4-methylbenzothiazole hydrochloride before step (b), wherein the 2-amino-4-methylbenzothiazole hydrochloride is separated, after the hydrochloric acid removal, from the reaction medium of step (a), wherein the base used in step (b) is in aqueous solution form, and wherein the 2-amino-4-methylbenzothiazole is separated from the reaction medium of step (b) after step (b) is completed.

14. Process as claimed in claim 13 wherein step (a) is conducted with stirring, wherein the hydrochloric acid is separated by boiling at reflux, wherein the 2-amino-4-methylbenzothiazole hydrochloride, after the hydrochloric acid separation is separated from the reaction medium of step (a) before step (b) by filtration, and wherein the separation of the 2-amino-4-methylbenzothiazole from the reaction medium of step (b) after step (b) is completed is achieved by filtration.

15. Process as claimed in claim 13 wherein the base is an alkali metal hydroxide.

16. Process as claimed in claim 13 wherein the base is an alkaline earth metal hydroxide.

17. Process as claimed in claim 14 wherein the base is sodium hydroxide, beryllium hydroxide, calcium hydroxide, lithium hydroxide or potassium hydroxide.

18. Process for the production of 2-amino-4-methylbenzothiazole consisting essentially of the steps of:
   (a) mixing o-tolylthiourea with methylene chloride to form a suspension, the methylene chloride also being a solvent for the o-tolylthiourea the suspension being formed at room temperature, and cooled to a temperature between −20° and +15° C.
   (b) reacting the o-tolythiourea with chlorine, a ring closure reactant, in the presence of the methylene chloride and in the absence of a catalyst, there being no chlorination of the benzene ring in the o-tolylthiourea, 2-amino-4-methylbenzothiazole hydrochloride resulting, one weight unit of o-tolylthiourea being used per 3 to 40 volume units of methylene chloride, 1 to 2 moles of chlorine being used per mole of o-tolylthiourea, step (b) being conducted with stirring, and step (b) being conducted with stirring, and step (b) being conducted at a temperature between −20° and +15° C., the methylene chloride being a solvent for the chlorine and being a suspending liquid for the 2-amino-4-methylbenzothiazole hydrochloride;
   (c) separating the hydrochloric acid, produced as a byproduct in step (b), from the 2-amino-4-methylbenzothiazole hydrochloride by boiling at reflux;
   (d) removing the 2-amino-4-methylbenzothiazole hydrochloride, after the hydrochloric acid removal, from the reaction medium of step (b) by filtration; and
   (e) reacting the 2-amino-4-methylbenzothiazole hydrochloride with a sufficient amount of a base, 2-amino-4-methylbenzothiazole resulting, said base being selected from the group consisting of an alkali metal hydroxide, an alkaline earth metal hydroxide, hydroxylamine, ammonium hydroxide and zinc hydroxide.

19. Process as claimed in claim 18 wherein the base is sodium hydroxide, beryllium hydroxide, calcium hydroxide, lithium hydroxide or potassium hydroxide.

20. Process as claimed in claim 18 wherein the base is sodium hydroxide.

* * * * *